United States Patent
Sullivan et al.

(10) Patent No.: US 9,815,754 B2
(45) Date of Patent: Nov. 14, 2017

(54) TRANSALKYLATION/DISPROPORTIONATION OR THERMAL HYDRODEALKYLATION HYDROCARBON PROCESSING METHODS AND SYSTEMS EMPLOYING AN INCREASED ETHYLBENZENE FEED CONTENT

(71) Applicant: UOP LLC, Des Plaines, IL (US)

(72) Inventors: Lawrence E. Sullivan, Mt. Prospect, IL (US); Emily Harrell, Chicago, IL (US); Feng Xu, Arlington Heights, IL (US); Jason L. Noe, Mt. Prospect, IL (US)

(73) Assignee: UOP LLC, Des Plaines, IL (US)

( * ) Notice: Subject to any disclaimer, the term of this patent is extended or adjusted under 35 U.S.C. 154(b) by 300 days.

(21) Appl. No.: 14/472,658

(22) Filed: Aug. 29, 2014

(65) Prior Publication Data

US 2016/0060189 A1 Mar. 3, 2016

(51) Int. Cl.
    C07C 4/16 (2006.01)
    C07C 4/14 (2006.01)
    C07C 7/04 (2006.01)
    C07C 7/09 (2006.01)
    C07C 6/12 (2006.01)

(52) U.S. Cl.
    CPC ............ *C07C 6/126* (2013.01); *C07C 4/16* (2013.01)

(58) Field of Classification Search
    CPC .................. C07C 6/126; C07C 4/16
    See application file for complete search history.

(56) References Cited

U.S. PATENT DOCUMENTS

| | | | | |
|---|---|---|---|---|
| 3,374,280 A | * | 3/1968 | Carr | C07C 4/16 585/488 |
| 4,150,061 A | * | 4/1979 | Feinstein | C10G 45/64 585/475 |
| 4,697,039 A | * | 9/1987 | Schmidt | C07C 15/08 585/475 |
| 4,761,514 A | | 8/1988 | Menard | |
| 4,783,568 A | * | 11/1988 | Schmidt | C07C 15/08 585/475 |
| 5,877,374 A | * | 3/1999 | Nacamuli | C07C 4/18 208/138 |
| 6,528,695 B1 | | 3/2003 | Magne Drisch et al. | |
| 7,241,930 B2 | | 7/2007 | Schlosberg et al. | |
| 7,709,692 B2 | | 5/2010 | Das et al. | |

(Continued)

OTHER PUBLICATIONS

Mamedov et al., Disproportionation of Ethylbenzenes by the Action of Aluminum Chloride, Neftekhimiya V12 N.4 518-22 (Jul.-Aug. 1972), v 12, n 4, p. 518-22, Jul. 1972; Language: Russian; ISSN: 00282421; Publisher: East View Publications.

*Primary Examiner* — Philip Louie (57) ABSTRACT

Methods and apparatus for processing hydrocarbons are provided. In one example, a method for processing hydrocarbons includes the step of providing feed stream including toluene, ethylbenzene, mixed xylenes, and $C_9$ hydrocarbons. Ethylbenzene is present in the feed stream in an amount of at least about 20% by weight of total $C_8$ aromatic hydrocarbons present in the feed stream. The method further includes the step of subjecting the feed stream to ethylbenzene conversion to form a benzene-containing product stream that includes benzene.

13 Claims, 3 Drawing Sheets

(56) References Cited

U.S. PATENT DOCUMENTS

| | | | | |
|---|---|---|---|---|
| 2006/0287563 A1* | 12/2006 | Schultz | ............... | C07C 5/2702 |
| | | | | 585/481 |
| 2007/0203387 A1* | 8/2007 | Glover | ..................... | C07C 2/66 |
| | | | | 585/831 |
| 2010/0069694 A1* | 3/2010 | Bogdan | ............... | C07C 5/2737 |
| | | | | 585/481 |

\* cited by examiner

TRANSALKYLATION/DISPROPORTIONATION OR THERMAL HYDRODEALKYLATION HYDROCARBON PROCESSING METHODS AND SYSTEMS EMPLOYING AN INCREASED ETHYLBENZENE FEED CONTENT

TECHNICAL FIELD

The technical field relates generally to hydrocarbon processing methods and apparatuses. More particularly, the technical field relates to hydrocarbon processing methods and apparatuses using transalkylation/disproportionation or thermal hydrodealkylation reactions wherein the ethylbenzene content in the feed stream to such reactions is relatively high.

BACKGROUND

Xylene isomers are produced in large volumes from petroleum as feedstocks for a variety of important industrial chemicals. The most important of the xylene isomer is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of $C_8$ aromatic hydrocarbons (the notation $C_x$ in the present disclosure is used to indicate hydrocarbon compounds having "x" carbon (C) atoms, as is conventional in the art).

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene and/or $C_{9+}$ aromatic hydrocarbons are de-alkylated to produce benzene or selectively disproportionated to yield benzene and $C_8$ aromatic hydrocarbons from which the individual xylene isomers are recovered.

$C_8$ aromatic hydrocarbons that are derived from hydrotreated and extracted pyrolysis gasoline ("pygas") have too great of an ethylbenzene content to be simply fractionated and sold as mixed xylenes (as used herein, the term "mixed xylenes" refers to a mixture of each of the three xylene isomers (ortho-, meta-, and para-) and ethylbenzene, which may or may not be in an equilibrium ratio). In the prior art, ethylbenzene has been super-fractionated from xylenes. However, this requires many fractionation trays (for example, possibly greater than 300) and high reflux rates (for example, possibly greater than 10 reflux vol./feed vol. (R/F)) to enable effective separation between ethylbenzene and para-xylene, which have only a 2° C. boiling point difference. Other aromatic hydrocarbon products from pygas include benzene, toluene, and $C_{9+}$ aromatic hydrocarbons, which must be accounted for and separated as well. While crude ethylbenzene can be valuable as a gasoline blending stock, as noted above, it is more valuable if it can be converted into a benzene product and also possibly an ethane product (which can be recovered as feed for a stream cracker).

Accordingly, it is desirable to provide improved methods and apparatuses for processing aromatic hydrocarbon feedstocks that include too much ethylbenzene for commercial sale. Furthermore, it is desirable to provide such methods and apparatuses that are capable of converting the ethylbenzene in such feedstocks to more valuable products, such as benzene, xylenes, and possibly also ethane. Still further, it is desirable to provide such methods and apparatuses that do not require the use of costly super-fractionation processes. Furthermore, other desirable features and characteristics of the presently disclosed embodiments will become apparent from the subsequent detailed description and the appended claims, taken in conjunction with the accompanying drawings and this background.

BRIEF SUMMARY

Methods and apparatus for processing hydrocarbons are provided. In one exemplary embodiment, a method for processing hydrocarbons includes the step of providing a feed stream including toluene, ethylbenzene, mixed xylenes, and $C_9$ hydrocarbons. Ethylbenzene is present in the feed stream in an amount of at least about 20% by weight of total $C_8$ aromatic hydrocarbons present in the feed stream. The method further includes the step of subjecting the feed stream to ethylbenzene conversion to form a benzene-containing product stream that includes benzene.

In another exemplary embodiment, an apparatus for processing hydrocarbons includes a separation system that 1) receives a feed stream that includes toluene, ethylbenzene, mixed xylenes, and $C_9$ hydrocarbons and 2) removes a portion of the toluene and a portion of the mixed xylenes from the feed stream. Ethylbenzene is present in the feed stream in an amount of at least about 20% by weight of total $C_8$ aromatic hydrocarbons present in the feed stream. The apparatus further includes a reactor system that receives the feed stream and forms a benzene-containing product stream that includes benzene, wherein the reactor system includes an ethylbenzene conversion unit that converts ethylbenzene from the feed stream to benzene and ethane.

In yet another exemplary embodiment, a process for upgrading hydrocarbons that includes the step of providing feed stream comprising toluene, ethylbenzene, mixed xylenes, and $C_9$ hydrocarbons. Ethylbenzene is present in the feed stream in an amount of at least about 20% by weight of total $C_8$ aromatic hydrocarbons present in the feed stream. The process further includes the steps of separating a portion of the toluene from the feed stream to reduce a toluene content of the feed stream and separating a portion of the mixed xylenes from the feed stream to reduce a mixed xylenes content of the feed stream. Still further, the process includes the steps of reducing an ethylbenzene content of the feed stream by subjecting the feed stream to a transalkylation/disproportionation reaction or to a thermal hydrodealkylation reaction to form a benzene-containing product stream that comprises benzene and unreacted ethylbenzene and separating a portion of the benzene from the benzene-containing product stream to reduce a benzene content of the benzene-containing product stream.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

The present disclosure is directed to various embodiments of methods and systems for processing aromatic hydrocarbon feedstocks using an ethylbenzene conversion unit operation such as but not limited to transalkylation/disproportionation or thermal hydrodealkylation reactions, to convert ethylbenzene to benzene and possibly also ethane (in the case of a transalkylation/disproportionation reaction), wherein the ethylbenzene content in the feed stream to such reactions is relatively high. Such methods and systems are capable of converting the ethylbenzene in such feedstocks to more valuable products, such as benzene and also possibly ethane. For example, according to the practice of the embodiments described herein, the value of upgrading ethylbenzene from gasoline blending value to benzene value outweighs the penalty in conversion across the catalysts due to the increased xylenes in the feed stream, and the higher level of ethylbenzene does not adversely affect xylenes equilibrium. Accordingly, xylene production across the transalkylation/disproportionation system will increase the total xylenes product and ethylbenzene dealkylation across the system will reduce the quantity of ethylbenzene that must be removed to fall within the maximum ethylbenzene fraction of the mixed xylene product, per the particular commercial specification as noted above (e.g., about 20% by weight).

In the present disclosure, various values of temperature, pressure, flow rates, number of stages, feed entry stage number, etc. are recited in association with the specific examples described below; those conditions are approximate and merely illustrative, and are not meant to limit the described embodiments. Additionally, for purposes of this disclosure, when the terms "middle", "top" or "lower" are used with respect to a column, these terms are to be understood as relative to each other, i.e. that withdrawal of a stream from the "top" of the column is at a higher position than the stream withdrawn from a "lower" portion of the column. When the term "middle" is used it implies that the "middle" section is somewhere between the "upper" and the "lower" section of the column. However, when the terms "upper", "middle" and "lower" have been used with respect to a distillation column it should not be understood that such a column is strictly divided into thirds by these terms.

Figure 1:
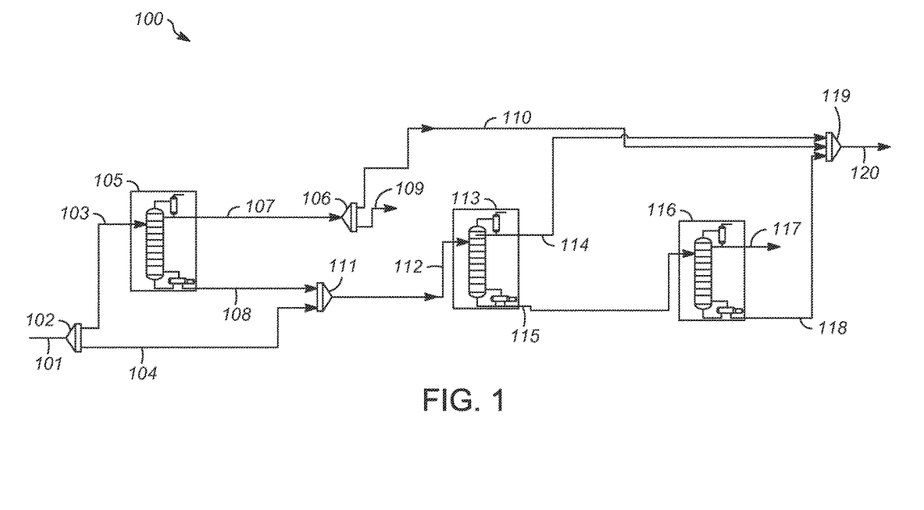
FIG. 1 is a schematic illustration of a system implementing a method for separating and recombining various aromatic hydrocarbons for use as a feedstock for subsequent transalkylation/disproportionation or thermal hydrodealkylation reactions in accordance with an exemplary embodiment.

FIG. 1 is a schematic illustration of a system 100 implementing a method for separating and recombining various aromatic hydrocarbons for use as a feedstock for subsequent ethylbenzene conversion, such as through transalkylation/disproportionation or thermal hydrodealkylation reactions, in accordance with an exemplary embodiment. System 100 uses as its feedstock a mixture of xylene isomers ("mixed xylenes") that also includes too much ethylbenzene to be commercially sold as mixed xylenes. That is to say, typical commercial specifications for mixed xylenes have a requirement for the maximum amount of ethylbenzene that may be included in the mixed xylenes, for example about 20% by weight maximum based on the overall weight of the $C_8$ aromatic hydrocarbon fraction. Accordingly, in one embodiment, system 100 includes a feed stream 101 that includes mixed xylenes (which may or may not be in equilibrium proportion) as well as a percentage of ethylbenzene that exceeds a given commercial mixed xylene specification, for example greater than about 20% wt. ethylbenzene based on the combined weight of all $C_8$ aromatic hydrocarbons present. In some instances, lower or higher percentages may be specified, such as greater than about 15% wt., or greater than about 25% wt. Other aromatic hydrocarbons may also be present in feed stream 101 including, for example, benzene, toluene, and $C_9$ and heavier aromatic hydrocarbons. Still further, other non-aromatic hydrocarbons may be included in feed stream 101. In one exemplary embodiment, feed stream 101 may be the net bottoms product from a benzene fractionation column from an upstream fractionation process. However, it will be appreciated that the exact composition of the feed stream 101 will depend significantly on the source of the feed stream 101.

For example, in one embodiment, feed stream 101 may result from a hydrotreated and extracted pygas stream. As is known in the art, products from pyrolysis or other cracking operations are generally hydrotreated according to conventional processes before being charged to a refining complex in order to remove sulfur, olefins, and other compounds that may affect product quality and/or damage catalysts used in processing such feedstocks. Light cycle oil from catalytic cracking also may be beneficially hydrotreated and/or hydrocracked according to known technology to yield products in the gasoline range; the hydrotreating preferably also includes catalytic reforming to yield the aromatics-rich feed stream. If the feed stream is catalytic reformate, the reformer preferably is operated at high severity to achieve high aromatics yield with a low concentration of nonaromatics in the product.

Regardless of its source and content, in an embodiment, stream 101 is split at stream splitter 102 into a first portion as stream 103 and a second portion as stream 104. One exemplary purpose of stream splitter 102 may be for operators who desire to make a separate toluene product (as described below) from feed stream 101; however, it is noted that splitter 102 is an optional component according to the present disclosure (in this regard, the percentage of the flow that may be "split" could vary anywhere from 0% to 100%, depending on process objectives). First portion stream 103 is directed to a distillation column 105 that separates first portion stream 103 into an overhead product that includes toluene and lighter (lower boiling) hydrocarbons and a bottom product that includes ethylbenzene and heavier (higher boiling) hydrocarbons. Accordingly, distillation column 105 may be colloquially known in the art as a "toluene column" due to its purpose in separating toluene from heavier hydrocarbons, particularly heavier aromatics such as ethylbenzene and xylenes. As noted above, since the separate product of toluene is optional, column 105 is also an optional component according to the present disclosure. As is conventional, toluene column 105 is illustrated including a primary distillation column, a condenser at a top end thereof, and a reboiler at a bottom end thereof. The operating conditions for toluene column 105 will also be appreciated by those having ordinary skill in the art. Toluene column 105 distributes its overhead product into overhead product stream 107, and it distributes its bottom product into bottom product stream 108. Overhead product stream 107 is split at stream splitter 106 to form an optional toluene product stream 109, which includes toluene and lighter hydrocarbons that are removed as a product of system 100, as well as a toluene stream 110 that remains within system 100 and serves as a balance line to allow constant flow through of stream 109, if provided, and that is eventually combined with other aromatic hydrocarbons to form a desired feed stream for use as a feedstock for subsequent ethylbenzene conversion.

In an embodiment and as further illustrated in FIG. 1, toluene column bottom product stream 108, which contains primarily $C_{8+}$ aromatic hydrocarbons but could also contain some toluene, is combined with the second portion stream 104 (split from original feed stream 101) in mixer 111 to form a combined stream 112 that includes all of the same hydrocarbons as feed stream 101 (due to second portion stream 104 being mixed in), but with a greater concentration of ethylbenzene and heavier hydrocarbons (due to toluene column bottom product stream 108 being mixed in). Combined stream 112 is then passed to a splitter column 113 that separates combined stream 112 into an overhead product that includes some ethylbenzene and lighter (lower boiling) hydrocarbons and a bottom product that includes some ethylbenzene, xylene, and heavier (higher boiling) hydrocarbons. Accordingly, distillation column 113 may be colloquially known in the art as an "ethylbenzene splitter" due to its purpose in distributing ethylbenzene into separate streams containing either lighter or heavier hydrocarbons. As used herein, the terms "heavier" and "lighter" with regard to hydrocarbons refer to hydrocarbons having a higher/lower vapor pressure. As is conventional, ethylbenzene splitter 113 is illustrated including a primary distillation column, a condenser at a top end thereof, and a reboiler at a bottom end thereof. The operating conditions for ethylbenzene splitter 113 will also be appreciated by those having ordinary skill in the art. Ethylbenzene splitter 113 distributes its overhead product into ethylbenzene-rich overhead product stream 114, and it distributes its bottom product into bottom product stream 115. This fractionation process is controlled so that the bottom product stream has about 20% or less (or whatever the particular specification may be) of ethylbenzene in the $C_8$ aromatic hydrocarbon product fraction thereof. Overhead product stream 114 remains within system 100, and the overhead product stream 114 is eventually combined with other aromatic hydrocarbons to form a desired feed stream for use as a feedstock for subsequent ethylbenzene conversion.

As further illustrated in FIG. 1, ethylbenzene splitter bottom product stream 115 115 is then passed to a distillation column 116 that separates stream 115 into an overhead product that includes xylenes and lighter (lower boiling) hydrocarbons and a bottom product that includes $C_9$ and heavier (higher boiling) hydrocarbons. Accordingly, distillation column 116 may be colloquially known in the art as a "xylenes column" due to its purpose in separating xylenes from heavier hydrocarbons, particularly $C_9$ and heavier aromatic hydrocarbons. According to the disclosure, this column 116 is optional, and is provided in the instance that it is desired to make a mixed xylene product for sale or further processing, or in the instance that $C_{9+}$ hydrocarbons are desired as a feed for further processes, such as the transalkylation/disproportionation reactions described below. As is conventional, xylenes column 116 is illustrated including a primary distillation column, a condenser at a top end thereof, and a reboiler at a bottom end thereof. The operating conditions for xylenes column 116 will also be appreciated by those having ordinary skill in the art. Xylenes column 116 distributes its overhead product into overhead product stream 117, and it distributes its bottom product into bottom product stream 118. Overhead product stream 117, which includes mixed xylenes, is removed as a product of system 100. Bottom product stream 118 remains within system 100, and that eventually will be combined with other aromatic hydrocarbons to form a desired feed stream for use as a feedstock for subsequent transalkylation/disproportionation or thermal hydrodealkylation reactions.

As initially noted above, each of toluene stream 110, ethylbenzene splitter overhead product stream 114, and xylenes column bottom product stream 118, are combined with other aromatic hydrocarbons to form a desired feed stream for use as a feedstock for subsequent ethylbenzene conversion. This combination may be effected using a mixer 119, which thereby forms a combined stream 120. Combined stream 120 therefore includes, primarily, toluene and any lighter hydrocarbons (derived from stream 110), ethylbenzene and any lighter hydrocarbons (derived from stream 114), and $C_9$ aromatics and any heavier boiling hydrocarbons (derived from stream 118). Some xylenes will also be present, due to the above-noted close boiling points of xylenes and ethylbenzene, originating from the ethylbenzene splitter overhead product stream 114; however, the amount of xylenes, on a relative basis, is reduced as compared to that present in feed stream 101. By appropriate selection of several parameters described above, the ultimate composition of stream 120 can be determined as desired for use as a feed stream in subsequent processes. These parameters includes, for example, the split ratio between streams 103 and 104, the split ratio between streams 109 and 110, and the size (number of trays) and operating conditions of the respective columns 105, 113, and 116, among others. For example, a greater amount of toluene in stream 120 may be realized by increasing the fraction of stream 107 that is split to stream 110. Further, a lesser amount of mixed xylenes may be realized by employing a relatively larger ethylbenzene splitter 113 and operating the column 113 at relatively higher reflux rates. Stream 120 is thereafter passed for further ethylbenzene conversion, e.g., in either a transalkylating/disproportionating system (described below with regard to FIG. 2) or a thermal hydrodealkylation system (described below with regard to FIG. 3).

Figure 2:
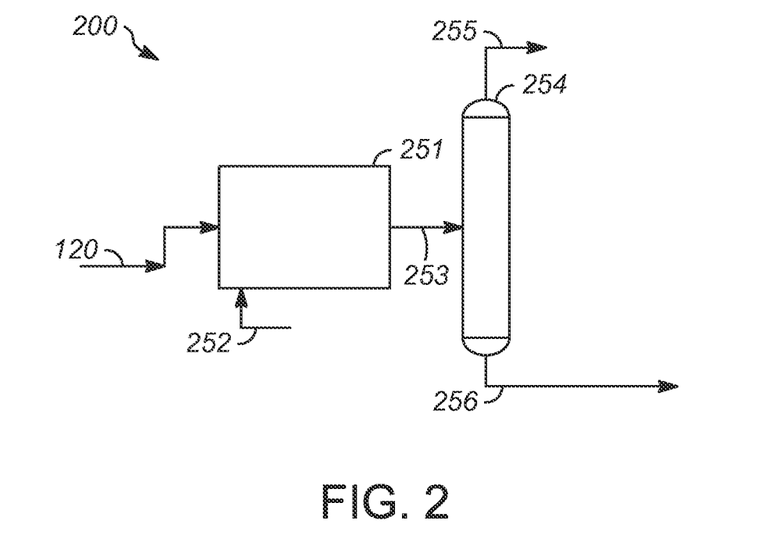
FIG. 2 is a schematic illustration of a system implementing a method for transalkylating/disproportionating the aromatic hydrocarbons produced by the system shown in FIG. 1 in accordance with another exemplary embodiment.

FIG. 2 is a schematic illustration of a system 200 implementing a method for converting ethylbenzene in the stream 120 by transalkylating/disproportionating the aromatic hydrocarbons produced by the system 100 shown in FIG. 1, and particularly those hydrocarbons from stream 120 of FIG. 1 as described above. As such, stream 120 is used as a feed for the transalkylation/disproportionation reactions of system 200, as will be described below. As shown in FIG. 2, stream 120 is passed to a transalkylation/disproportionation zone 251. The feed to the transalkylation/disproportionation zone includes the toluene (and possibly lighter hydrocarbons) that originates from stream 110 of FIG. 1, as well as $C_9$ and aromatics that originate from stream 118 of FIG. 1. $C_{10+}$ hydrocarbons may also be present, as well as some amount of mixed xylenes and ethylbenzene, as noted above. As generally known in the art, any transalkylation/toluene disproportionation process converts toluene and $C_{9+}$ aromatics into more valuable benzene and equilibrium mixed xylenes. Ethyl-substituted alkylbenzenes (i.e., ethylbenene, methyl-ethylbenzenes and diethlybenzenes) have the ethyl group(s) cracked from the benzene ring at high conversion per pass across the transalkylation catalysts. In conventional systems, the $C_8$ aromatics (ethylbenzene and xylenes) in the feed stream (i.e., stream 120) are limited so that they do not hinder the equilibrium reactions. However, according to the practice of the embodiments described herein, the value of upgrading ethylbenzene from gasoline blending value to benzene value outweighs the penalty in conversion across the catalysts due to the increased xylenes in the feed stream 120, and the higher level of ethylbenzene does not adversely affect xylenes equilibrium. Accordingly, xylene production across the transalkylation/disproportionation system 200 will increase the total xylenes product and ethylbenzene dealkylation across the system 200 will reduce the quantity of ethylbenzene that must be removed to fall within the maximum ethylbenzene fraction of the mixed xylene product, per the particular commercial specification as noted above (e.g., about 20% by weight).

With continued reference to FIG. 2, the stream 120 is fed to the transalkylation/disproportionation reaction zone 251. Stream 120 is subjected to the disproportionation and transalkylation reactions in the presence of hydrogen (provided via stream 252, which may be about 80% pure $H_2$ to greater than about 99.9% pure $H_2$, with other $C_1$ through $C_6$ hydrocarbon impurities that do not participate in the reaction) in the reaction zone 251. The reactions in the reaction zone 251 proceed in the presence of catalysts. The catalysts employed in the reaction zone 251 may be one or more catalysts known in the art for these purposes, for example, a metal-containing zeolite. Of the catalyst, the metal may be one or more selected from the following group: Bi, Mo, Fe, Co, Ni, Pt, Ag, Pd, Re and Au; and the zeolite may be one or more selected from the following group: Y-type zeolite, mordenite, β-zeolite and ZSM-type zeolite. During reactions, the pressure may be from about 1.0 to about 5.0 MPa, the temperature may be from about 300 to about 480° C., and hydrogen/hydrocarbon molar ratio may be from about 1 to about 10. The space velocity by weight may be maintained at about 0.5 to about 10 $h^{-1}$. The products of the disproportionation and transalkylation reactions are removed from the reaction zone 251 via the stream 253.

A stripper column 254 is provided to further process product stream 253. Stripper column 253 removes light ends (for example, hydrocarbons lighter than benzene) as an overhead fraction 255, and a bottom product stream 256 is transferred for further processing according to the system described in greater detail below with regard to FIG. 4. The overhead fraction 255 may be an ethane-rich vent gas, which may find value as use as a feed to a stream cracker, for example such as may be used to produce pygas as a byproduct of the production of ethylene/propylene. The bottom product stream 256 includes primarily benzene and xylenes, as well as any unconverted toluene, ethylbenzene, and $C_{9+}$ hydrocarbons. Of course, the relative amounts of each depend greatly on the composition of the feed stream 120, as well as on the operating conditions of the reaction zone 251.

Figure 3:
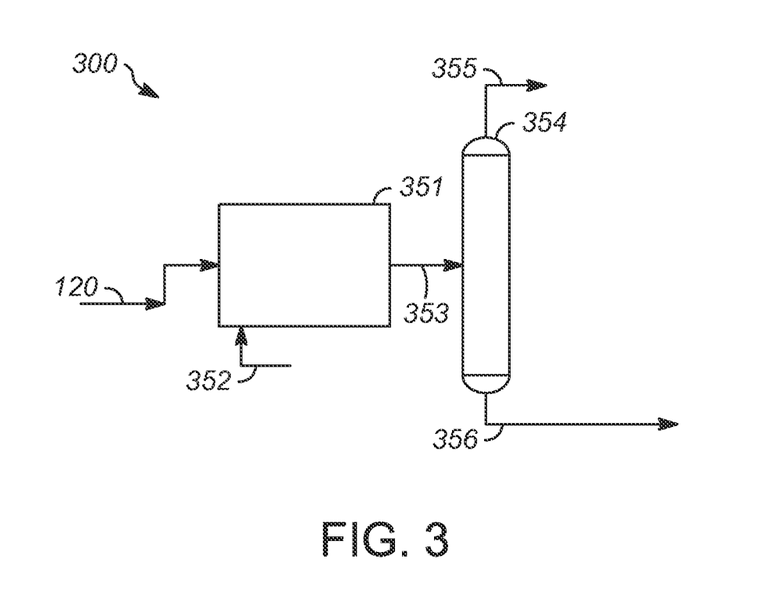
FIG. 3 is a schematic illustration of a system implementing a method for thermal hydrodealkylating the aromatic hydrocarbons produced by the system shown in FIG. 1 in accordance with an exemplary embodiment.

In accordance with an alternative embodiment of the present disclosure, FIG. 3 is a schematic illustration of a system 300 implementing a method for ethylbenzene conversion by thermal hydrodealkylating the aromatic hydrocarbons produced by the system shown in FIG. 1, namely those hydrocarbons in stream 120 produced in FIG. 1. The hydrodealkylation reaction produces benzene from alkyl aromatic hydrocarbons, namely $C_{7-9}$ aromatic hydrocarbons. The benzene-forming conditions are preferably sufficient to dealkylate at least about 70, such as at least about 85, for example from about 85 and 98, mass-percent of the aromatic hydrocarbons found in stream 120.

Accordingly, as shown in FIG. 3, stream 120 is passed to a hydrodealkylation reaction zone 351. In general, hydrodealkylation conditions include elevated temperatures and pressures, e.g., from about 200 to about 700° C. and about 0.1 MPa(g) to about 5.0 MPa(g) and the presence of hydrogen, e.g., from about 1:1 to about 50:1 moles of hydrogen per mole of aromatic hydrocarbons. The hydrogen may be provided to the thermal hydrodealkylation reaction zone 351 via stream 352. Exemplary thermal hydrodealkylation conditions are described in, for instance, W. L. Liggin, UOP Thermal Hydrodealkylation (THDA) Process, in Handbook of Petroleum Refining Processes, Second Edition (1997), at pp. 2.23 to 2.26.

A benzene product stream 353 is generated as a result of subjecting the stream 120 to benzene-forming conditions as described above within reaction zone 351. This stream will contain benzene and conversion products of the dealkylation. Lighter hydrocarbons such as methane, ethane, propane, and the like that have been removed from the phenyl ring may be separated from the benzene in the benzene product stream 353 by distillation, including flash distillation, in distillation column 354. These lighter hydrocarbons may be removed from system 300 via distillation column overhead stream 355, whereas the benzene product and any unconverted heavier alkyl aromatic compounds may be transferred for further processing as a bottom product stream 356 according to the system described in greater detail below with regard to FIG. 4. The bottom product stream 356 includes primarily benzene, as well as any unconverted toluene, xylenes, ethylbenzene, and $C_{9+}$ hydrocarbons. Of course, the relative amounts of each depend greatly on the composition of the feed stream 120, as well as on the operating conditions of the reaction zone 351.

According to the foregoing, it will be appreciated that whether the embodiment according to FIG. 2 or the embodiment according to FIG. 3 is selected for use to process stream 120 depends on the desired product composition. As described above, transalkylation/disproportionation favors a relatively higher percentage of mixed xylenes in the product stream 256, whereas thermal hydrodealkylation favors a relatively higher percentage of benzene in the product stream 356.

Figure 4:
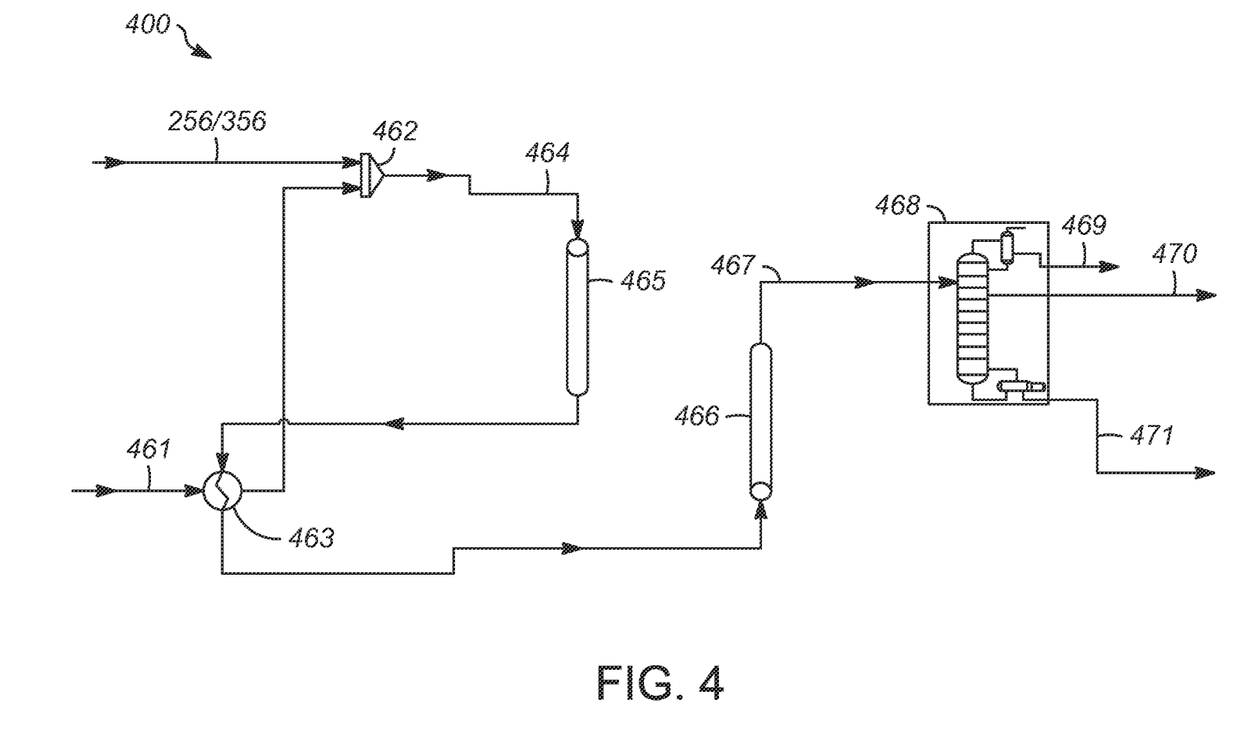
FIG. 4 is a schematic illustration of a system implementing a method for separating the reaction products of the transalkylation/disproportionation or thermal hydrodealkylation reactions shown in FIGS. 2 and 3, respectively.

The processing of either stream 256 or stream 356, depending on the embodiment employed, continues with regard to FIG. 4, which is a schematic illustration of a system 400 implementing an optional method for separating the reaction products of the transalkylation/disproportionation or thermal hydrodealkylation reactions shown in FIGS. 2 and 3, respectively. As an initial matter, it should be noted that streams having the same or similar composition as stream 256/356 may be incorporated with stream 256/356 for purposes of efficiency in processing and/or for purposes of heat exchange. By way of example, the source of one possible stream 461 may be the extract derived from an extractive distillation process that extracts benzene and toluene from a naphtha reformate stream. Such processes include, for example the Sulfolane™ process licensed by UOP LLC of Des Plaines, Ill., USA. Additional stream 461 may be used to exchange heat with other process streams, such as shown by heat exchanger 463 in FIG. 4, whereafter it may be joined with the stream 256/356 for further processing, using for example mixer 462. Stream 461 may thus provide a source of "fresh" $C_6$ to $C_{9+}$ aromatic hydrocarbons to the separation system shown in FIG. 4.

Combined stream 464 produced by mixer 462 thereafter proceeds downstream for treatment in one or more clay treatment units 465, 466 (of course, it should be noted that the combination with stream 461 is not necessary for the practice of the described embodiments, in which case the combined stream 464 would merely be stream 256/356). As is known in the art, clay treatment units 465, 466, if present, may be provided for the removal of any alkylates and olefins that may be present in the stream 464, as is known in the art. The clay treatment units 465, 466 may be configured in any known manner suitable for this purpose. For example, heat exchanger 463 may be positioned between the individual clay treatment units 465, 466, in an embodiment. Stream 467 leaving the clay treatment unit 466 may thus include the hydrocarbons compounds as described above with regard to streams 256/356 with alkylate and olefin compounds substantially (such as greater than about 90%) removed therefrom.

Clay treated stream 467 is then directed to a distillation column 468 that separates stream 467 into a side-cut product that includes primarily benzene and a bottom product that includes toluene and heavier (higher boiling) hydrocarbons, most particularly the mixed xylenes that may have been produced as a reaction product according to FIG. 2 if such embodiment were employed. Accordingly, distillation column 468 may be colloquially known in the art as a "benzene column" due to its purpose in separating benzene from heavier hydrocarbons, particularly heavier aromatics such as toluene. Benzene column 468 may also include an overhead product, which would therefore include hydrocarbons lighter than benzene, if present. As is conventional, benzene column 468 is illustrated including a primary distillation column, a condenser at a top end thereof, and a reboiler at a bottom end thereof. The operating conditions for benzene column 468 will also be appreciated by those having ordinary skill in the art. Benzene column 468 distributes its overhead product into overhead product stream 469, its side-cut (benzene) product into side-cut product stream 470, and it distributes its bottom product into bottom product stream 471. Each of streams 469-471 is then removed from system 400 for further processing and/or use as such. Such further processing may include further refining or filtering steps, for example.

In general, the processes and systems described in FIG. 4 pertaining to clay treating, heat exchange, and variations of benzene fractionation are well known in the art, and as such should be considered optional components of the described embodiments. Other alternates would also be suitable.

Accordingly, described herein are various embodiments of methods and systems for processing aromatic hydrocarbon feedstocks using transalkylation/disproportionation or thermal hydrodealkylation reactions wherein the ethylbenzene content in the feed stream to such reactions is relatively high. Such methods and systems are capable of converting the ethylbenzene in such feedstocks to more valuable products, such as benzene and ethane.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:

1. A process for upgrading hydrocarbons comprising the steps of:
   providing a feed stream comprising toluene, ethylbenzene, mixed xylenes, and $C_9$ hydrocarbons, wherein ethylbenzene is present in the feed stream in an amount of at least about 20% by weight of total $C_8$ aromatic hydrocarbons present in the feed stream;
   dividing the feed stream into a first portion and a second portion in a first stream splitter;
   separating the first portion of the feed stream in a first separation column into a first overhead stream and a first bottoms stream, the first overhead stream comprising toluene and lighter hydrocarbons and the first bottoms stream comprising ethylbenzene and heavier hydrocarbons;
   dividing the first overhead stream into a first portion and a second portion in a second stream splitter;
   combining the first bottoms stream and the second portion of the feed stream into a first combined stream;
   separating the first combined stream in a second separation column into a second overhead stream and a second bottoms stream, the second overhead stream comprising ethylbenzene and lighter hydrocarbons, and the second bottoms stream comprising ethylbenzene, xylenes, and heavier hydrocarbons;
   separating the second bottoms stream in a third separation column into a third overhead stream and a third bottoms stream, the third overhead stream comprising xylenes and lighter hydrocarbons and the third bottoms stream comprising $C_9$ and heavier hydrocarbons;
   combining the first portion of the first overhead stream, the second overhead stream and the third bottoms stream into a second combined stream; and
   converting at least a portion of the second combined stream into benzene in an ethylbenzene conversion zone to form a reaction product stream containing benzene.

2. The process of claim 1 further comprising:
   separating the reaction product stream in a fourth separation column into an overhead fraction and a benzene containing product stream.

3. The process of claim 2 further comprising:
   separating the benzene containing product stream in a fifth separation column into at least a benzene stream.

4. The process of claim 2 wherein the ethylbenzene conversion zone comprises a transalkylation/disproportionation zone and wherein the overhead fraction comprises an ethane rich gas.

5. The process of claim 2 wherein the ethylbenzene conversion zone comprises a thermal hydrodealkylation zone and wherein the overhead fraction comprises at least one of methane, ethane, and propane.

6. The process of claim 1 wherein the ethylbenzene conversion zone comprises a transalkylation/disproportionation zone and the reaction product stream further comprises xylenes.

7. The process of claim 1 wherein the reaction product stream further comprises unreacted ethylbenzene.

8. The process of claim 1 wherein at least one of the first, second, and third separation columns comprises a distillation column, a fractionation column, a splitter column, or combinations thereof.

9. The process of claim 1 wherein the second bottoms product stream comprises about 20% by weight or less of ethylbenzene.

10. The process of claim 1 wherein the first combined stream has a higher concentration of ethylbenzene and heavier hydrocarbons than the feed stream.

11. The process of claim 1 wherein the second combined stream has a lower concentration of xylenes than the feed stream.

12. The process of claim 1 further comprising increasing an amount of toluene in the second combined stream by increasing the first portion of the first overhead stream.

13. The process of claim 1 wherein the feed stream comprises a hydrotreated and extracted pygas stream.

* * * * *